United States Patent
Langguth

[19]

[11] Patent Number: 6,048,317
[45] Date of Patent: Apr. 11, 2000

[54] METHOD AND APPARATUS FOR ASSISTING A USER IN POSITIONING AN ULTRASONIC TRANSDUCER

[75] Inventor: Alfred Langguth, Hudson, N.H.

[73] Assignee: Hewlett-Packard Company, Palo Alto, Calif.

[21] Appl. No.: 09/157,010

[22] Filed: Sep. 18, 1998

[51] Int. Cl.$^7$ .................................................. A61B 8/02
[52] U.S. Cl. ..................... 600/449; 600/443; 600/447; 600/407
[58] Field of Search .................................. 600/437, 443, 600/447, 455, 549, 382, 407; 378/205, 206

[56] References Cited

U.S. PATENT DOCUMENTS

| | | | |
|---|---|---|---|
| 5,419,332 | 5/1995 | Sabbah et al. | 600/455 |
| 5,551,434 | 9/1996 | Iinuma | 600/455 |
| 5,645,066 | 7/1997 | Gandini et al. | |
| 5,873,830 | 2/1999 | Hossack et al. | 600/447 |

*Primary Examiner*—Marvin M. Lateef
*Assistant Examiner*—Ali M. Imam

[57] ABSTRACT

An imaging system incorporating the invention includes a transducer for scanning an imaging beam through a region of interest (ROI) which includes a structure or function to be imaged on a display, such as an anatomical structure or a hemodynamic function. A processor is responsive to a changes in the image that are caused by changes in imaging beam position, to calculate at least a first measure of a feature of the structure or function and to cause the display to manifest the first measure by a first indication. The processor may also be responsive to a further change in the image brought about by movement of the imaging beam, to calculate at least a second measure of the feature and to cause the display to manifest the second measure by a second indication. The user is thereby able to determine by display of the first and second indications, of the relative difference in positions of the transducer. The processor also determines from a plurality of scans of the imaging beam, an extreme (or target) one of plural ones of the first measure and causes the first indication to manifest the extreme (or target) one of the plural ones of the first measure. Such display enables a user to know how much to reposition the imaging beam so as to assure that the first measure is at the extreme or target value.

14 Claims, 3 Drawing Sheets

METHOD AND APPARATUS FOR ASSISTING A USER IN POSITIONING AN ULTRASONIC TRANSDUCER

FIELD OF THE INVENTION

This invention relates to the field of medical imaging and, more particularly, to a method and apparatus for enabling improved user placement of an ultrasound transducer.

BACKGROUND OF THE INVENTION

The use of ultrasonic imaging for medical diagnostic purposes is well known. In particular, ultrasound has been used for many years to aid in the diagnosis of certain cardiac and vascular diseases. In addition, Doppler ultrasound technology has been recognized as an important tool in the evaluation of blood flow information. In Doppler ultrasound imaging, a reflection from a stationary object provides a signal at zero frequency shift (that is, at the intermediate frequency). The Doppler frequency shift in the echo signal returned from a moving target varies monotonically with the instantaneous velocity of the target. A review of cardiac Doppler measurement technology is contained in R. G. O'Connell, Jr., "The Role of Doppler Ultrasound in Cardiac Diagnosis," Hewlett-Packard Journal, June 1986 at pp 20–25, and in P. A. Magnin, "Doppler Effect: History and Theory, Id. at pp 26–31; in L. Halberg et al., "Extraction of Blood Flow Information Using Doppler-Shifted Ultrasound, Id. at pp 35–40; and in B. F. Hunt et al., "Digital Processing Chain for A Doppler Ultrasound Subsystem, Id. at pp 45–48.

A typical prior art medical ultrasound imaging system employs a phased array or mechanical transducer, a scanner unit and a signal processing and display unit. The scanner unit, for example, provides analog signal conditioning, beamforming and signal translation from the ultrasound frequency range to a more convenient intermediate frequency (I.F.) range. The processing and display unit then converts the I.F. signals to digital samples and processes the digital samples in order to facilitate extraction and display of desired information contained in the echo signals.

The display and processing unit may provide both black and white (monochrome) and color imaging information. The monochrome mode typically is used to show anatomic detail, with blood flow shown in the color mode. In a typical system, a two-dimensional monochrome image may show a sector-shaped or rectangular scan region of a patient, displayed at a rate of approximately 30 frames per second. A color mode image may be overlaid on a portion (up to 100%) of the scanned sector, supplementing the monochrome image. At each picture element (pixel) on the display, either the monochrome signal or the color signal is displayed; or alternatively, the two signals may be combined.

The color image is typically a color-coded blood flow map, where the color coding indicates localized velocity and/or turbulence of blood flow. In an exemplary commercial system, velocity is shown in shades of red and blue, with red indicating flow toward the transducer and blue indicating flow away from the transducer, or vice versa. Sometimes another color may be mixed in over a portion of the scale to focus attention on flows within selected ranges. The intensity and/or shading of the color represents the speed of the flow towards or away from the transducer. Shades of green are sometimes added to indicate turbulence.

While the ultrasound image provides a qualitative representation of the region of interest, it is frequently desirable to obtain quantitative measurements of vessel parameters, such as blood velocity, vessel diameter and vessel wall directions. In order to determine blood velocity, the angle between the ultrasound beam direction and the direction of the blood vessel must be determined. A method for adjustment of Doppler angle in ultrasound images is disclosed in European Patent Application No. 0 755 920 published May 28, 1997. This published application describes a technique for calculating the direction of the vessels blood flow and coordinates of the vessel walls in the vicinity of a cursor when the cursor is positioned inside of a vessel in the ultrasound image.

U.S. Pat. No. 5,645,066 to Gandini et al. describes a medical ultrasound imaging system which employs displayed indicators and measure bars to enable the user to better control a displayed image. More particularly, a scanning guide is displayed and changed in accord with which frame of a group of images is being displayed. Further, the scanning guide can show the capacity of an image memory and how much of that capacity has been utilized.

Known techniques for quantitatively determining parameters, such as blood velocity and vessel diameter from ultrasound images have been relatively difficult to use and, even after measurements are taken, it has been difficult to determine their accuracy. The accuracy of such a measurement is dependent upon such factors as the positioning of the scanned ultrasound beam with respect to the structure being imaged. For instance, an accurate measure of the diameter of a vessel must be obtained to assure that the cross-section of the vessel and the blood flow volume therethrough is properly calculated. Once such a calculation is performed, it is thereafter difficult to determine if the transducer was appropriately positioned to enable the measurement of the maximum diameter dimension. Further, such techniques have required relatively skilled operators and do not produce consistent results.

In co-pending U.S. patent application Ser. No. 09/187,013, entitled "Automated Measurement and Analysis of Patient Anatomy Based on Image Recognition" to J. S. Nikom, and assigned to the same Assignee as is this Application, a method is described for measurement and analysis of patient's anatomy which generates an ultrasound image of a region of a patient and provides coordinates of walls of a vessel in the image. One or more parameters of the vessel in the vicinity of a cursor are determined from the wall coordinates and are recorded. The vessel parameters may include vessel diameter, vessel center coordinates and/or vessel wall directions. A center of gravity of an upper vessel wall and a center of gravity of a lower vessel wall are determined from the wall coordinates. The vessel diameter and the vessel center coordinates are determined from the centers of gravities of the upper and lower vessel walls.

The cursor is then to be moved to the vessel center coordinates in the ultrasound image and rotated into alignment with the vessel wall directions. The cursor is then moved along the vessel in the cursor direction to a new position and the process of determining one or more vessel parameters is performed at the new cursor position. By repeating this process, the vessel is automatically mapped. The disclosure of the aforementioned copending patent application is incorporated herein by reference.

To further improve upon the teachings of the above-noted copending patent application, it is desirable to provide methods and apparatus for confirming a user's proper positioning of an ultrasound transducer in relation to a structure being imaged, after the image has been acquired. More particularly, it is desirable to reduce the amount of training necessary to obtain such measurements from ultrasound images; to reduce or eliminate the variability of results from different ultrasound operators; and to enable such measurements to be obtained rapidly.

SUMMARY OF THE INVENTION

An imaging system incorporating the invention includes a transducer for scanning an imaging beam through a region of interest (ROI) which includes a structure or function to be imaged on a display, such as an anatomical structure or a hemodynamic function. A processor is responsive to a changes in the image that are caused by changes in imaging beam position, to calculate at least a first measure of a feature of the structure or function and to cause the display to manifest the first measure by a first indication. The processor may also be responsive to a further change in the image brought about by movement of the imaging beam, to calculate at least a second measure of the feature and to cause the display to manifest the second measure by a second indication. The user is thereby able to determine by display of the first and second indications, of the relative difference in positions of the transducer. The processor also determines from a plurality of scans of the imaging beam, an extreme (or target) one of plural ones of the first measure and causes the first indication to manifest the extreme (or target) one of the plural ones of the first measure. Such display enables a user to know how much to reposition the imaging beam so as to assure that the first measure is at the extreme or target value.

BRIEF DESCRIPTION OF THE DRAWINGS

For a better understanding of the present invention, reference is made to the accompanying drawings in which.

DETAILED DESCRIPTION OF THE PREFERRED EMBODIMENT

Figure 1:
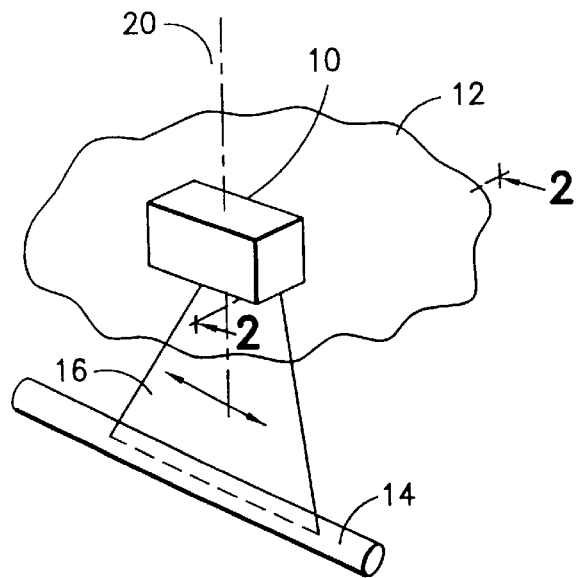
FIG. 1 is a schematic perspective view of an ultrasound transducer that is being used to image a vessel.

Referring to FIG. 1., an ultrasound transducer 10 is positioned on a surface 12 of a patient (shown only partially) and transmits ultrasound energy into a target region within the patient and receives reflected ultrasound echo's from various structures, tissues and organs within the target region. One such structure is a vessel 14. As will be understood from the description below, one use of transducer 10 is to enable the calculation of blood flow volume through vessel 14 through use of a detection of blood flow velocities and correlation thereof with a calculated cross-section of vessel 14.

Figure 2:
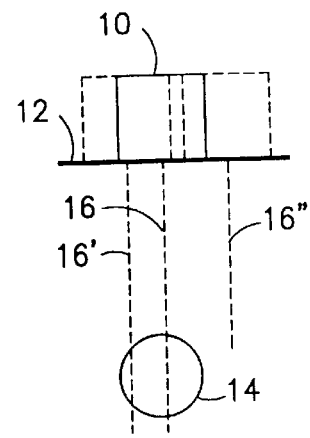
FIG. 2 is a view of the ultrasound transducer of FIG. 1 from the perspective of arrows 2—2.

Transducer 10 includes an array of transducer elements (not shown) and, by appropriately delaying pulses applied to each transducer element, produces a focused ultrasound beam that is scanned in a plane 16. Scan plane 16 extends orthogonally from transducer 10 and, if transducer 10 is perfectly aligned with vessel 14 (see FIG. 2), scan plane 16 perfectly bisects the largest (i.e., central) diameter of vessel 14, thereby enabling precise determination of the diameter thereof and, through further calculations, its cross sectional area. However, if transducer 10 is positioned so that scan plane 16 is parallel to artery 14 but is offset (e.g., scan plane 16') from the center line thereof, the resulting image will display a spacing between vessel walls that is less than maximum due to the offset of the scan plane 16'. Further, if transducer 10 is moved even further away, scan plane 16" may completely miss vessel 14. Lastly, if transducer 10 (see FIG. 1) is rotated by the user about its center line 20, scan plane 16 will be caused to intersect vessel 14 at an angle. Thus, assuming scan plane 16 still remains within artery 14 after rotation of ultrasound transducer 10 about center line 20, any measurements taken to determine the diameter of vessel 14 will very likely be in error and will cause further errors in the corresponding velocity and blood flow measurements.

Figure 3:
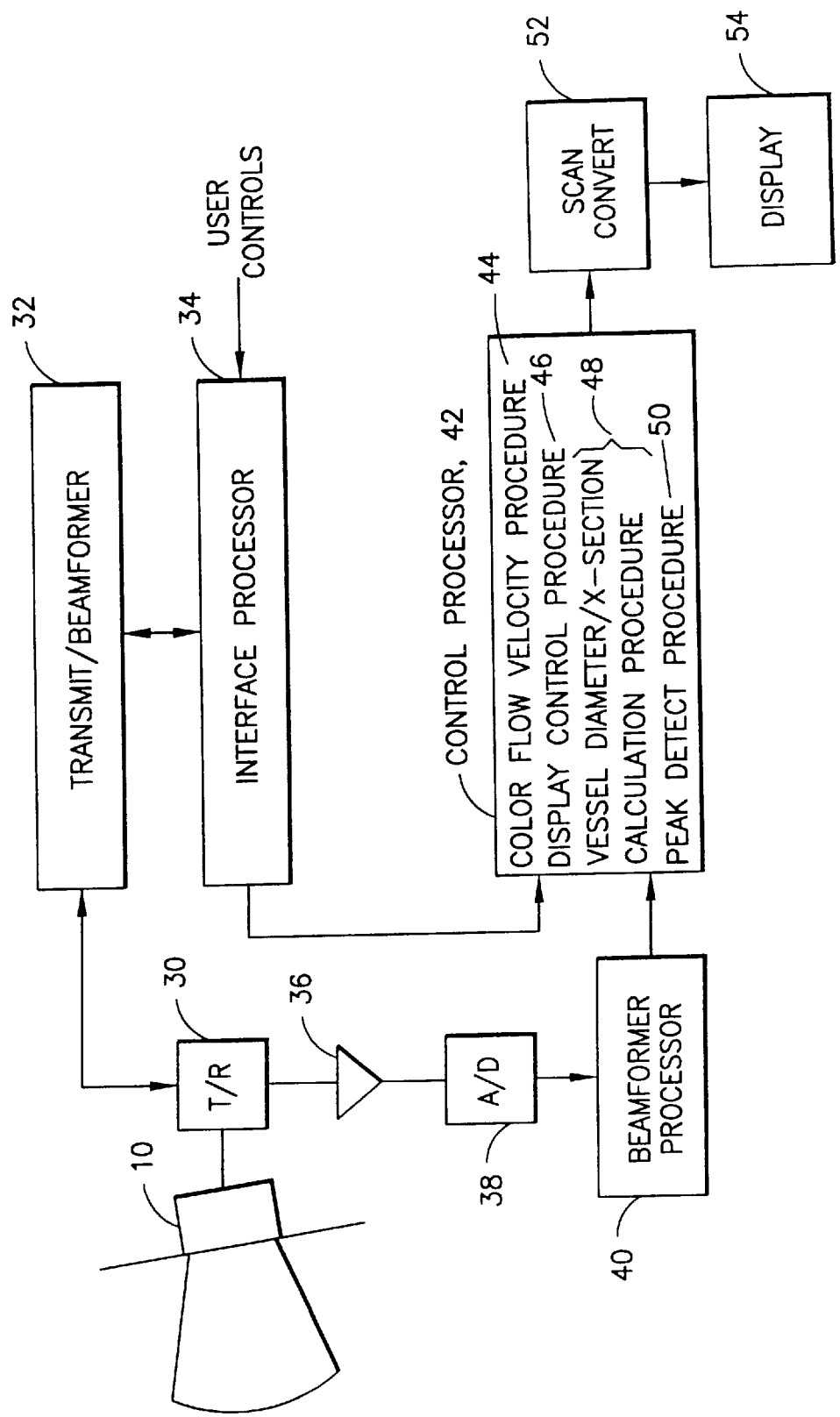
FIG. 3 is a simplified block diagram of an ultrasound imaging system suitable for incorporation of the present invention.

Referring to FIG. 3, a high-level block diagram of an ultrasound system adapted to perform the invention is illustrated. Ultrasound transducer 10 is coupled via a transmit/receive coupler 30 to a transmit/beam former module 32 which is, in turn, controlled by interface processor 34 to produce both imaging and Doppler signals. Received echo's are converted within ultrasound transducer 10 to electrical signals which are supplied by a transmit/receive coupler 30, amplifier 36 and analog-to-digital (A/D) converter 38 to a beam former processor 40. The delayed signals from each transducer element are summed in beam former processor 40 to provide a scan signal that represents the reflected energy levels along given scan lines within scan plane 16. The process is repeated for multiple scan lines to provide signals which enable the generation of an image of the target region containing vessel 14. The scan pattern may be a sector scan, wherein scan lines originate at the center of ultrasound transducer 10 and are directed at different angles therefrom. A rectangular scan pattern can also be utilized.

Beam former processor 40 feeds the resulting image to control processor 42 which performs a number of functions with respect to the received image. Control processor 42 operates in response to various control inputs from interface processor 34 which, in turn, is responsive to user inputs. Control processor 42 includes a colorflow velocity procedure 44 which is responsive to a user input to implement a blood flow velocity measurement within artery 14. Control processor 42 further includes a display control procedure 46 which will be described in detail below. Briefly stated, display control procedure 46 enables display of both an image of artery 14 (see FIG. 4) and one or two measure bars which define both maximum determined diameters of an imaged vessel and current measured diameters of the vessel.

Vessel diameter/cross section calculation procedure 48 calculates plural vessel diameters and vessel cross sections at respectively selected diameter positions. Lastly, peak detect procedure 50 detects a maximum diameter value(s) that is/are measured when the user moves ultrasound transducer 10 across vessel 14.

Blood flow volume measurements are dependent upon both an accurate blood velocity measurement and accurate vessel diameter and cross section area calculations. All of the aforesaid measurements and calculations are further dependent upon accurate positioning of ultrasound transducer 10 to assure that image plane 16 is in alignment with vessel 14, in addition to being centered with respect thereto. In prior art blood velocity measurements, the user positions a cursor within the imaged blood vessel (which appears as a pair of approximately parallel, but displaced light-colored lines). Blood flow is imaged as a dark field and, if overlaid with color, manifests various colorations in accordance with flow velocities and/or turbulence.

The cursor direction is aligned with the blood flow direction in the vessel and is used to determine a Doppler angle. That angle is then used to calculate blood velocity in accordance with (i) the transducer's output frequency, (ii) the sensed Doppler frequency shift and (iii) the cosine of the Doppler angle.

In above-mentioned European Patent Application 0 755 920 A1, a vessel analysis algorithm is described which has the ability to both calculate vessel flow direction and the coordinates of the vessel wall in the vicinity of the cursor when the cursor is placed inside the vessel being imaged. The user places the cursor inside the vessel using a track ball control and initiates a vessel analysis algorithm. The algorithm calculates the vessel flow direction and rotates the cursor on the display to align with the flow direction. In the co-pending application of Nikom, a method and apparatus for automated cursor positioning and rotation are described and enable the determination of both vessel wall positions and a distance D between the imaged vessel walls. However, if the ultrasound image plane 16 is not centered on the vessel, the distance D is not equal to the maximum vessel diameter.

Figure 4:
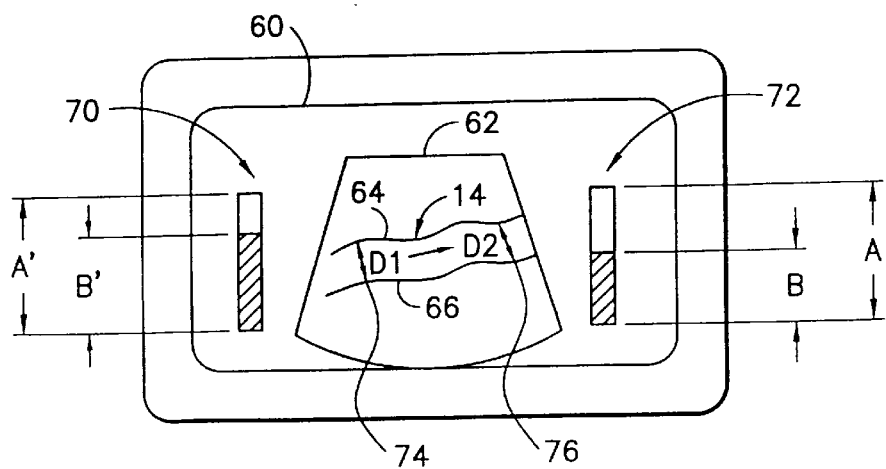
FIG. 4 is a display that is presented to assist the user in positioning the ultrasound transducer of FIG. 1.

To assure proper positioning of ultrasound transducer 10, display control procedure 46, via scan convert module 52 and display 54, causes presentation on display 54 of an image such as is shown FIG. 4. Presented on screen 60 is an ultrasound image 62 that includes vessel 14 that appears as an upper wall 64 and a lower wall 66. As can be understood (see FIG. 2), if a user moves transducer 10 in such a manner that scan plane 16 moves from right to left, or vice-versa, across vessel 14, the distance between upper imaged wall 64 and lower imaged wall 66 changes. Further, if ultrasound transducer 10 is not positioned so that image plane 16 is parallel to vessel 14, upper imaged wall 64 and lower imaged wall 66 will not be displayed as parallel (or substantially parallel) lines, but rather will either diverge or converge, as the case may be.

As will be further understood from the description below, the invention calculates diameters D1 and D2 at two positions (e.g., 74, 76) along vessel 14. A pair of measure bars 70 and 72 (e.g., gauges) are positioned on opposed sides of ultrasound image 62 and each provides two measures of diameters D1 and D2. More specifically, measures A and A' indicate the maximum diameters of vessel 14, as determined by the user scanning image plane 16 through vessel 14 from side to side. In other words, measures A and A' indicate the maximum determined diameters of vessel 14 at points 74 and 76. Measures B and B' provide an indication of current measured distances D1 and D2, as illustrated by ultrasound display 62. Different measure indications of B and B' inform the user that image plane 16 is not positioned parallel to vessel 14. The user, by rotating and/or tilting ultrasound transducer 10, can alter measures B and B', with one increasing while the other decreases until both are approximately equal. At such time, the user can assume that image plane 16 is substantially parallel to vessel 14.

However, at such time, image plane 16 may still be offset from the center of vessel 14. By then moving ultrasound transducer 10 from right to left or vice-versa across vessel 14, measures B and B' can be made to either increase, concurrently, or decrease, concurrently. Once they are made approximately equal to measures A and A' (the maximum diameters), the user can be assume that image plane 16 is properly aligned with the center line of vessel 14. Accordingly, at this position, diameter measurements can be obtained and volumetric blood flow calculated. Further, by saving the image at the time such a blood flow measurement is taken, one who subsequently examines the calculation results and the saved image can be assured, by measure bars 70 and 72, and the coextensive heights of A', B' and A, B, of the proper positioning of image plane 16. Thus, measure bars 70 and 72 serve as confirmation of the accuracy of the determined diameters and calculated cross sectional areas of vessel 14.

Figure 5:
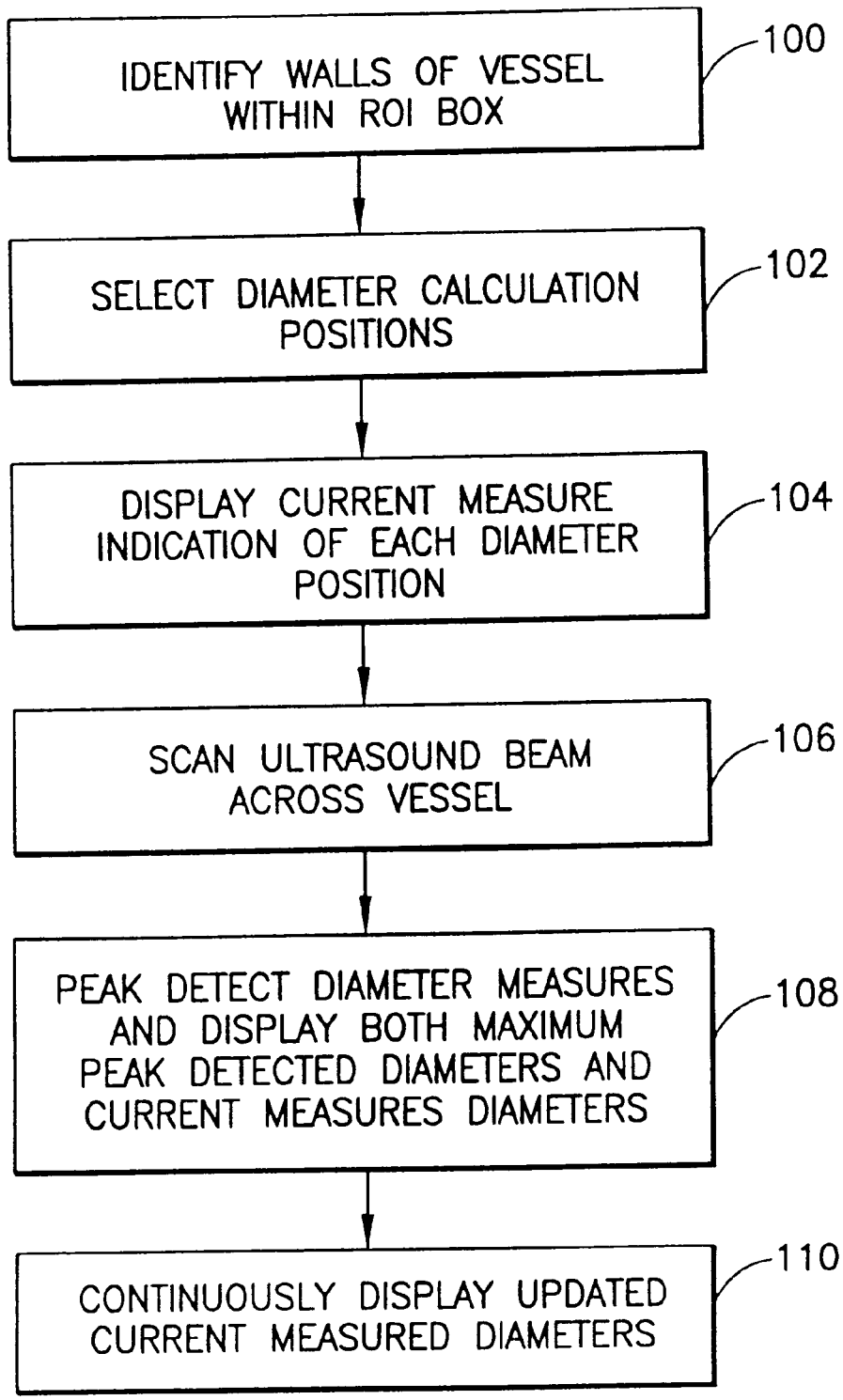
FIG. 5 is a high level logic flow diagram illustrating the method of the invention.

Turning now to FIG. 5, a flow diagram illustrates the method of the invention. Initially, the user establishes a region of interest (ROI) box about the vessel to be imaged and initiates a procedure to identify the walls of the vessel within the ROI box (step 100). Note that the ROI can be the entire image. Thereafter, the user, by positioning a cursor at locations along the imaged vessel, selects positions along the vessel at which diameters are to be calculated. Thereafter, vessel diameter/cross section calculation procedure 48 is invoked and calculates vessel diameters at the selected vessel positions (step 102). Display control procedure 46 then causes display 54 to display the current measure indications of each calculated diameter (step 104).

Next, the user is instructed to move ultrasound transducer 10 across the vessel so that scan plane 16 is enabled to completely interrogate the vessel, from side to side (step 106). During each scan of the ultrasound beam within image plane 16, vessel diameter/cross section calculation procedure 48 calculates new vessel diameters. As will be understood by those skilled in the art, the calculated diameters change in accordance with the position of scan plane 16 vis-a-vis the center line of vessel 14.

After ultrasound transducer 10 has been moved across vessel 14, peak detection procedure 50 detects a maximum calculated diameter (or a target or extreme value thereof) at each of points 74 and 76 of the vessel and causes measure bars 70 and 72 to display diameters A and A' as the maximum diameters determined during the scan action (step 108). Thereafter, display control procedure 46 continually updates diameter measures B and B' in accordance with the user's positioning of ultrasound transducer 10 (step 110). The user is enabled to know when ultrasound transducer 10 is optimally positioned by observing when measures A' and B' are approximately equal to measures A and B, respectively. Under such conditions, image plane 16 is substantially parallel to the direction of the vessel and is centered thereon. At such time, appropriate Doppler and volumetric flow measurements can be taken.

It should be understood that the foregoing description is only illustrative of the invention. Various alternatives and modifications can be devised by those skilled in the art without departing from the invention. For instance, while the invention has been described in the context of an ultrasound system, it is equally useful in any real time imaging system where the user has the ability to reposition an imaging device in accord with a displayed image and/or measure indication, e.g., MRI and CAT scans. Further, while measure bars 70 and 72 have been used to illustrate the invention, other measure manifestations may be used, e.g., a "gas gauge", numeric indications, etc. Further, while the preferred embodiment displays plural measures of an anatomical feature, a further embodiment may display only a single measure, thus requiring the user to remember an optimum measure of the anatomical feature, while repositioning the ultrasound transducer. Also, for this instance, a vessel's maximum diameter is generally desired to be measured, but for other applications, it may be desired to locate a minimum diameter or another specified dimension. Also the invention is applicable to images that include not only 1-D and 2-D image data sets but also 3-D and 4-D image data sets.

Accordingly, the present invention is intended to embrace all such alternatives, modifications and variances which fall within the scope of the appended claims.

I claim:

1. An imaging system comprising:

imaging means for passing an imaging beam through a region of interest (ROI) which includes a structure or function to be imaged;

display means for displaying said structure or function;

processor means responsive to relative movements between said imaging means and said ROI and resulting signals from said ROI, for calculating at least first measures of a feature of said structure or function and for causing said display means to concurrently display said first measures by a first indication that is continuously updated in accord with signal changes from said ROI which occur as a result of said relative movements, said first indication being displayed in conjunction with an image of said structure or function.

2. The imaging system as recited in claim 1, wherein said processor means is responsive to further relative movements between said imaging means and said ROI, for calculating at least a second measure of said feature and for causing said display means to display said second measure by a second indication, said second indication being displayed in conjunction with an image of said structure or function, said user thereby able to determine by display of said first indications and said second indication, an optimum value of said measure of said feature.

3. The imaging system as recited in claim 1, wherein said processor means, in response to said relative movements between said imaging means and said ROI, determines a maximum one of plural ones of said first measure and causes said first indication to manifest said maximum one of said plural ones of said first measure.

4. The imaging system as recited in claim 3, wherein said processor means, in response to said relative movements of said imaging means with respect to said ROI, calculates first measures of said feature at plural locations of said structure and causes said display means to display said first measures by plural first indications, said processor means also responsive to further relative movements of said imaging means with respect to said ROI, for calculating at least second measures of said feature at plural locations and for causing said display means to display said second measures by second indications.

5. The imaging system as recited in claim 2, wherein said processor means causes said display means to display said first indications by a graphic indicator, a numeric value, a color manifestation or a combination thereof and to further display said second measure as a graphic indicator, a numeric value, a color manifestation or a combination thereof to enable ready comparison therebetween.

6. The imaging system as recited in claim 1, wherein said imaging means is an ultrasound transducer, said structure to be imaged is a vessel and said first measure is a diameter value of said vessel.

7. The imaging system as recited in claim 2, wherein said imaging means is an ultrasound transducer, said structure to be imaged is a vessel, said first measure is a diameter value of said vessel and said second measure is a maximum diameter or another specified dimensional value of said vessel.

8. A method for assisting a user to position an imaging beam during imaging of a region of interest (ROI) which includes a structure or function to be imaged, said method comprising the steps of:

responding to movements of said imaging beam and resulting signals from said ROI, by calculating at least a first measure of a feature of said structure or function; and b) causing simultaneous display of said first measure by a first indication, said first indication being displayed in conjunction with an image of said structure or function.

9. The method as recited in claim 8, further comprising the steps of:

1) responding to a further movement of said imaging beam by calculating at least a second measure of said feature; and d) causing simultaneous display of said second measure by a second indication, said second indication being displayed in conjunction with an image of said structure or function, said display of said first indication and second indication thereby enabling s aid user to determine a relative difference in positions of said image beams.

10. The method as recited in claim 9, wherein step a), in response to movements of said imaging beam and resulting signals from said ROI, determines a determined one of plural ones of said first measure, and step b) causes said first indication to manifest said determined one of said plural ones of said first measure.

11. The method as recited in claim 10, wherein step a), in response to said movements of said imaging beam and resulting signals from said ROI, calculates first measures of said feature at plural locations of said structure or function, and step b) displays said first measures by plural first indications, and step c) is responsive to further movement of said imaging beam to calculate at least second measures of said feature at plural locations and step d) displays said second measures by second indications, whereby said user is able to determine by display of said first indications and second indications a relative difference in positions of said imaging beams.

12. The method as recited in claim 11, wherein step b) displays said first indications as plural graphic indications of maxima of said first measures and step d) displays said second measures as juxtaposed graphic indications to enable ready comparison thereof by said user.

13. The method as recited in claim 11, wherein step b) displays said first indications as plural alphanumeric indications of maxima of said first measures and step d) displays said second measures as juxtaposed alphanumeric indications to enable ready comparison thereof by said user.

14. The method as recited in claim 11, wherein steps c) and d) enable a continuous display of changes in said second measures as said imaging beam is moved relative to said ROI.

* * * * *